United States Patent [19]

Pontifex

[11] 4,296,749

[45] Oct. 27, 1981

[54] COLOSTOMY APPLIANCE

[75] Inventor: Edward J. Pontifex, Virginia Beach, Va.

[73] Assignee: Louis B. Fine, Norfolk, Va. ; a part interest

[21] Appl. No.: 170,057

[22] Filed: Jul. 18, 1980

[51] Int. Cl.³ .............................................. A61F 5/44
[52] U.S. Cl. .................................................... 128/283
[58] Field of Search ........................ 128/283, 294, 295

[56] References Cited

U.S. PATENT DOCUMENTS

| | | | |
|---|---|---|---|
| 2,054,535 | 9/1936 | Diack | 128/283 |
| 2,516,391 | 7/1950 | Jolly | 128/283 |
| 2,667,167 | 1/1954 | Raiche | 128/283 |
| 3,055,368 | 9/1962 | Baxter | 128/283 |
| 3,683,918 | 8/1972 | Pizzella | 128/283 |

FOREIGN PATENT DOCUMENTS 2550766  5/1977  Fed. Rep. of Germany ...... 128/283

Primary Examiner—C. Fred Rosenbaum
Attorney, Agent, or Firm—Shanley, O'Neil & Baker

[57] ABSTRACT

An improved colostomy appliance includes a first pouch for receiving solid and liquid waste and a second separable pouch for containing gas. The two pouches are connected by a releasable coupling which provides a gas flow path therebetween and which includes valve structure for automatically closing each pouch upon disconnection of the two pouches.

17 Claims, 5 Drawing Figures

U.S. Patent      Oct. 27, 1981      4,296,749
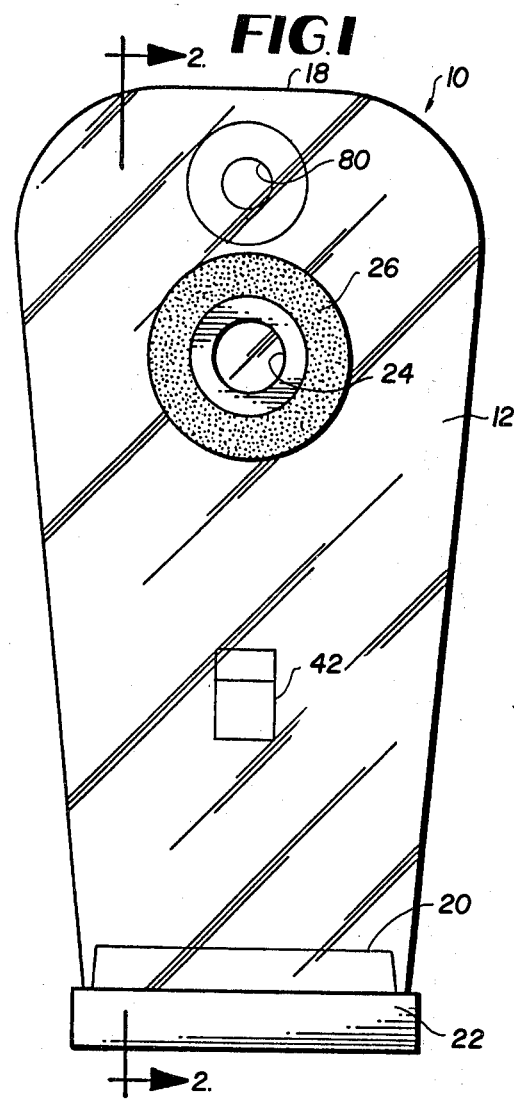
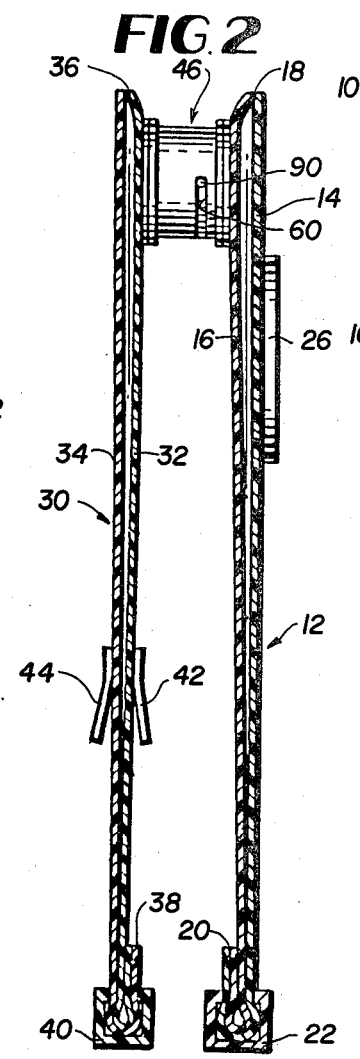
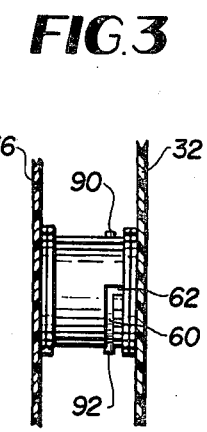
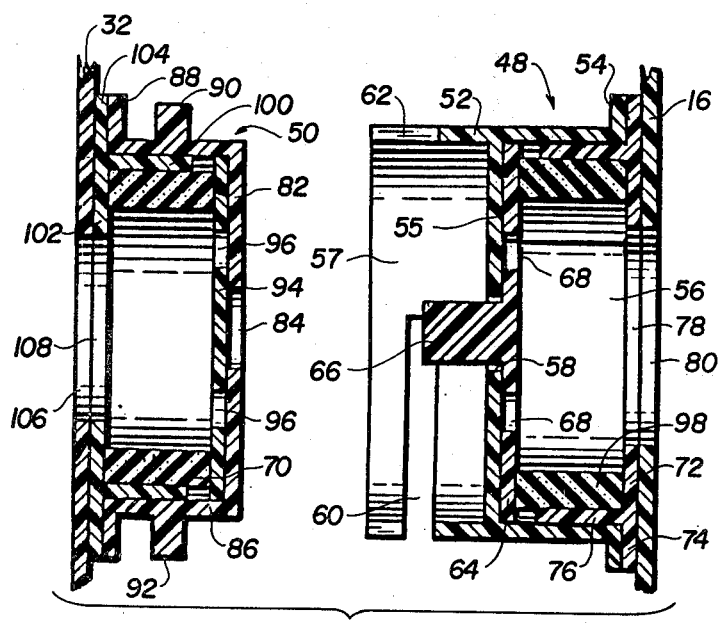

COLOSTOMY APPLIANCE

BACKGROUND OF THE INVENTION

1. Field of the Invention

This invention relates to colostomy appliances and more particularly to a colostomy appliance having an improved closable gas collecting means.

2. Description of the Prior Art

The accumulation of gas in colostomy bags, or pouches, and the escape of gas from such pouches has presented difficulties and embarrassment to persons using the device, and numerous devices have been developed in an effort to solve the problem. Initially, it was the practice to provide small openings near the top of such pouches to permit the escape of gas more or less continuously. While this arrangement generally avoided discomfort resulting from pressure in the pouch, it nevertheless was not satisfactory in that venting could not be controlled and the escaping gas was frequently embarrassing.

U.S. Pat. No. 3,055,368 to Baxter discloses a colostomy drainage pouch including an integral vent in the form of a labyrinth-type seal at the top designed to facilitate the discharge of gas upon squeezing or applying pressure to the pouch. This seal arrangement theoretically avoided the escape of liquids which was a further problem with the prior pouches having simple punctures or openings at the top. While this arrangement was an improvement, it nevertheless presented a problem in that the venting of gas could not always be controlled.

A colostomy bag apparatus employing a manually operable gas escape valve is disclosed in U.S. Pat. No. 2,054,535 to Diack. This apparatus also includes a gas filter having a filling of activated charcoal or other suitable chemical material intended to reduce odors of gas escaping through the filter when the vent valve is opened.

U.S. Pat. No. 2,667,167 to Raiche discloses a colostomy pouch including a separate gas collecting bag in the form of an inflatable rubber balloon-like sack, attached to a rigid vent by stretching its mouth onto a fixed nipple. An elastic band retained the sack in place. A difficulty with this arrangement, however, was that excessive gas pressure was required in the waste collecting pouch to inflate the gas collecting sack. Further, no means was provided for closing the vent or for closing the gas collecting sack when removed from the vent.

SUMMARY OF THE INVENTION

It is a primary object of the present invention to provide an improved colostomy appliance including a first pouch for the collection of liquid and solid waste and a second or gas collecting pouch connected to the first by an improved coupling means providing free gas flow into the gas collecting pouch.

Another object of the present invention is to provide means for automatically closing the coupling means to prevent the unintended escape of gas from the gas pouch and the waste pouch when the coupling means is disconnected.

Another object is to provide such an appliance in which the coupling means includes valve means which is automatically opened upon connecting the two pouches and closed upon separation of the two pouches.

In the attainment of the foregoing and other objects and advantages, an important feature of the invention resides in providing a waste collecting pouch adapted to be adhesively or otherwise attached to the body of the person using the device in the conventional manner, and providing a second, separate pouch of convenient size and shape adapted to be connected to the waste collecting pouch at a point near its top. The pouches each include coupling means adapted to be joined together to provide a gas flow path therethrough to the joined pouches. Each coupling means includes valve means which is automatically closed when the two are uncoupled and automatically opened when the two are coupled. The gas pouch preferrably includes tab means on its opposed surfaces to facilitate expansion to produce a vacuum tending to draw gas from the waste pouch into the gas pouch. Both pouches preferrably have their bottoms open and are proivded with conventional removable closure means to facilitate emptying and cleaning.

BRIEF DESCRIPTION OF THE DRAWINGS

The foregoing and other objects and advantages of the invention will become apparent from the detailed description contained hereinbelow, taken in conjunction with the drawings, in which:

FIG. 1 is an elevation view of a colostomy appliance embodying the present invention;

FIG. 2 is a sectional view taken on line 2—2 of FIG. 1;

FIG. 3 is a fragmentary sectional view taken on 3—3 of FIG. 2;

FIG. 4 is an exploded view, on an enlarged scale, of the coupling and valve means shown in FIGS. 2 and 3; and FIG. 5 is a view similar to FIG. 4 and showing the components in the coupled state.

DESCRIPTION OF THE PREFERRED EMBODIMENTS

Referring now to the drawings in detail, a colostomy appliance embodying the present invention is designated generally by the reference numeral 10 and includes a first pouch 12 for receiving liquid and solid waste. As is conventional, pouch 12 is formed from a thin, flexible, substantially impervious synthetic resin sheet and includes inner and outer panels 14, 16, respectively joined along their edges to define the pouch having a sealed or closed top end 18 and an opened bottom end 20. Although the synthetic sheet employed in the manufacture of such pouches is normally translucent or opaque, it is illustrated in FIG. 1 as being transparent to simplify the disclosure.

A resilient clamping element 22, of conventional construction, is provided to releasably close the open bottom end 20 of pouch 12 to provide a liquid-tight container, with the clamp 22 being easily removable for emptying and cleaning purposes. The inner panel 14 is provided with an annular opening 24 on its vertical centerline and at a point spaced downward from the closed top end 18. An annular ring 26 of adhesive material is bonded directly to the outer surface of inner panel 14 around the opening 24 to provide means for attachment directly to the skin to the person using the appliance. Alternate, known attaching means may, of course, be employed.

The colostomy appliance 10 also includes a second pouch 30 for the collection of gas. Pouch 30 is generally similar to pouch 12, and includes inner and outer panels of thin, resilient, synthetic resin material edge sealed to provide a pouch having a closed top 36 and an open bottom 38. A second resilient clamping element 40 is employed to releasably close the open end 38. A pair of flexible pull tabs 42, 44 respectively are adhered to the outer surface of panels 32, 34 respectively, at a central location thereon and in substantially opposed relation to one another. Tabs 42, 44 may be grasped and pulled away from one another to separate the flexible panels 32, 34 thereby creating a partial vacuum in the closed bag 30 to exhaust gases from the pouch 12 in the manner described hereinbelow.

Pouches 12 and 30 are releasably joined adjacent their top ends by a coupling assembly indicated generally at 46. Coupling assembly 46 comprises a female subassembly 48 permanently attached as by bonding or heat sealing to the outer panel 16 of pouch 12 adjacent the closed top 18 of the pouch, and a male subassembly 50 similarly attached to the inner panel 32 of pouch 30 at a corresponding position adjacent the closed top 36. The respective positions of the subassemblies may be reversed, i.e., subassembly 48 may be mounted on panel 32 and subassembly 50 may be mounted on panel 16, if desired.

As best seen in FIG. 4, coupling subassembly 48 includes a hollow, generally cylindrical body member 52 having a radially outwardly extending flange 54 integrally formed on the one end and an integrally formed, transversly extending diaphgram 55 located within the body 52 at a point substantially equally spaced from the open ends thereof. Diaphragm 55 divides the interior of cylindrical body 52 into two substantially equal, open-ended chambers 56, 57 and has a central, axial opening 58 formed therein, providing communication between chambers 56, 57. A pair of circumferentially extending slots 60 are formed in the cylindrical body 52 in spaced relation to the end opposite the flange 54, with the slots being in diametrically opposed relation to one another and each extending approximately 90 degrees around the circumference of the body 52. Each slot 60 terminates at one end in an axial portion 62 (see FIG. 3) extending to the open end of the cylindrical body 52.

An annular valve disc 64 having a diameter slightly less than the internal diameter of cylindrical body 52 is slidably mounted within chamber 56. A rigid axially extending finger 66 extends through the opening 58 and diaphragm 55, with the diameter of the finger 66 being substantially less than that of the opening 58. A plurality of gas flow passages 68 are also formed in the valve disc in outwardly spaced relation to the finger 66 and in outwardly spaced relation to the opening 58.

Valve disc 64 is normally urged into contact with the diaphragm 56 by a resilient rubber-like annular ring 70 having one end bearing directly on the flat surface of the disc and its other end bearing on a radially extending flange 72 of a retaining member which includes an outwardly extending flange 74 overlying and rigidly bonded to the flange 54, and an axially extending annular skirt 76 telescoped within the end of the cylindrical body 52. The axial length of the skirt 76 is less than the distance from the flange 54 to the diaphragm 55 so that valve disc 64 can move axially within the chamber 56, against the resilient force of the annular ring 70 from the normally closed position shown in FIG. 4 to the open position wherein the valve disc engages and it stopped by the end of skirt 76 as shown in FIG. 5.

The outer surface of retaining member flanges 72, 74 are bonded directly to the outer surface of panel 16 of pouch 12, with the opening 78 defined by the inner periphery of flange 72 overlying and communicating with a hole 80 in panel 16.

The connector subassembly 50 comprises a substantially cup-shaped body member including a generally planar end panel 82 having a central opening 84 extending therethrough and a cylindrical sidewall 86 integrally formed with panel 82. Sidewall 86 terminates at its open end in an outwardly extending radial flange 88. A pair of diametrically opposed, radially outwardly extending, generally cylindrical locking post 90, 92 are integrally formed on the outer surface of cylindrical sidewall 86.

A valve disc 94 having a diameter slightly smaller than that of the internal diameter of the sidewall 86 is received within the cup-shaped valve body and is normally retained in overlying contacting relation with the end panel 82. Valve disc 94 has a plurality of openings 96 formed therethrough in outwardly spaced relationship from the central opening 84 of the end panel 82. A resilient annular ring of rubber-type material 98 normally retains valve disc 94 in contact with end panel 82, and the resilient ring 98 is retained in the cup-shaped body member 50 by a retaining member having a cylindrical annular skirt element 100 telescopingly received in the open end of the cup-shaped valve body and an inwardly directed flange 102 overlying the end of the resilient ring. A second, substantially coplanar flange 104 overlies and is rigidly bonded to the outwardly directed surface of the flange 88 on the cup-shaped body member.

The outwardly directed surfaces of flanges 102, 104 are firmly attached to the outer surface of panel 32 of pouch 30. An opening 106 in panel 32, adjacent the closed top end 36 of the pouch 30 overlies a corresponding opening 108 defined by the inner periphery of the flange 102 to provide free communication between the interior of pouch 30 and interior of the cup-shaped subassembly 50. As shown in FIGS. 4 and 5, the annular skirt 100 has an axial length less than that of the annular sidewall 86, with the end of the skirt 100 acting as a stop to limit movement of the valve disc 94 away from the end wall 84.

The coupling assembly 46 may be assembled by telescoping the male subassembly 50 into the open end of the female subassembly 48 and aligning the lugs 90, 92 with the opposed open end portions 62 of slot 60. As the subassembly 50 is pressed into subassembly 48, the end of the finger 66 will project through openings 58 and 85 and engage the valve disc 94. Further telescoping movement will compress the resilient rings 70 and 98 until the valve discs 64 and 94 are spaced from the diaphragm 55 and the end wall 82, respectively, as shown in FIG. 5. Since movement of each valve disc is limited by the respective retaining elements, opening of both valve discs is assured. In the open position, a free flow patch for gas is provided through the openings 68 in valve disc 64, the opening 58 in diaphragm 56, opening 84 in end wall 82, and the openings 96 in valve disc 94. Thus, gas is free to flow from the waste pouch 12 into the gas pouch 30 when the gas pouch is assembled onto the waste pouch. However, when the gas pouch is removed, the respective valve discs close the coupling subassemblies to seal the associated pouch. When the subassembly 50 is fully inserted into the chamber 57 of subassembly 48, pouch 30 and the subassembly 50 is rotated approximately 90 degrees, with the lugs 90, 92 sliding in slot 60 to firmly lock the two pouches together. In this position, the outer surface of cup-shaped subassembly 50 fits closely within chamber 57 to effectively seal the assembly to prevent the escape of gas.

In normal use of the colostomy appliance, gas will accumulate in both pouch 12 and in pouch 30 since their interiors are in free fluid communication through the open valves of the coupling assembly 46. When it is desired to dispose of accumulated gas, pull tabs 42 and 44 can be manually separated or pulled apart to expand pouch 30 thereby tending to draw gas from pouch 12 to pouch 30. If desired, light pressure may be applied to pouch 12 to assure substantially complete transfer of the gas to pouch 30. Pouch 30 may then be rotated through 90 degrees and the force of the resilient rings will quickly separate the two pouches and automatically close the respective valve members to prevent the escape of gas from either pouch. The gas from pouch 30 can then be released at a convenient place by removing the resilient clamp 40 from the open end 38. Thereafter, the pouch can be resealed and the gas pouch reinstalled for repeated use.

From the above description, it will be apparent that the colostomy appliance of the present invention will provide adequate reserve volume for the accumulation and retention of gas for a substantial length of time without causing discomfort to the person using the device as a result of excess pressure within the pouch. Since the appliance is completely sealed, the problem of embarrassment due to odors of escaping gas is avoided. Further, when the connector assembly is uncoupled, both pouches are completely sealed so that, when necessary, the waste pouch may be used independently of the gas pouch for short periods.

While the connector assembly is illustrated as a relatively massive bulky structure, this is for purposes of illustration only and in practice the assembly will be a relatively thin, compact unit which can readily be concealled beneath the clothing of the person using the appliance. Also, for economy, it is contemplated that a single pouch 30 may be packaged for sale with a number of pouches 12 since the pouch 30 may be repeatedly used.

It should also be understood that, while specific connector assembly and valve structure has been disclosed and described, various modifications of this structure and of the configuration of the pouches may be made without departing from the inventive concept. Accordingly, while a preferred embodiment of the invention has been disclosed and described, it should be understood that the invention is not so limited but rather that it is intended to include all embodiments which come within the spirit and scope of the invention.

I claim:

1. A colostomy appliance comprising, in combination,
   a first pouch formed from first and second imperforate wall members of flexible plastic material connected together to form a flexible generally flat elongated container having a closed top and an open bottom,
   an inlet opening formed in the first sheet of the first pouch in downwardly spaced relation to the closed top,
   attaching means surrounding the inlet opening for attaching the first pouch to the body of the person using the appliance,
   a gas outlet opening formed in the second sheet of the first pouch adjacent the closed top thereof,
   means for closing the open bottom end of the first pouch,
   a second pouch formed from flexible synthetic resin sheet material and having a gas inlet opening therein, and
   coupling means for releasably connecting the gas inlet opening of the second pouch to the gas outlet opening of the first pouch and providing a sealed gas flow path therebetween,
   the coupling means including valve means for closing the gas outlet opening and the gas inlet opening when the gas inlet opening of the second pouch is not connected to the gas outlet opening of the first pouch.

2. The colostomy appliance according to claim 1 wherein the coupling means comprises,
   a first coupling member on the first pouch,
   a second coupling member on the second pouch, and
   fastener means for releasibly joining the first and second coupling members to releasibly connect the first and second pouches.

3. The colostomy appliance according to claim 2 wherein the valve means comprises a valve in the coupling member on each pouch.

4. The colostomy appliance according to claim 3 wherein the valve in the coupling member on each pouch comprises resilient means normally biasing the valves to the closed position to prevent the flow of gas therethrough.

5. The colostomy appliance according to claim 4 further comprising means for opening the valves in the coupling members on each pouch when the coupling members are releasibly connected together.

6. The colostomy appliance according to claim 5 further comprising pull tab means on the synthetic sheet material of the second pouch to facilitate manual expansion of the second pouch to draw gas from the first pouch.

7. The colostomy appliance according to claim 6 wherein the second pouch is formed from first and second sheets of flexible synthetic resin material edge sealed together and is of substantially the same size and configuration as the first pouch.

8. The colostomy appliance according to claim 7 wherein the outlet opening in the first pouch is located between the inlet opening and the closed top.

9. The colostomy appliance according to claim 8 wherein the second pouch has an open bottom end, and further comprising means for closing the open bottom end of the second pouch.

10. The colostomy appliance according to claim 9 wherein the attaching means comprises an annular ring of adhesive material surrounding the inlet opening and bonded to the outer surface of the first sheet of the first pouch, the adhesive material being capable of adhering directly to the skin of a person using the appliance.

11. A colostomy appliance comprising, in combination,
    a first pouch formed from first and second flexible sheets of synthetic resin material edge sealed together to form a flexible generally flat, elongated container having a closed top and an open bottom,
    an inlet opening formed in the first sheet of the first pouch in downwardly spaced relation to the closed top,
    attaching means surrounding the inlet opening for attaching the first pouch to the body of the person using the appliance, a gas outlet opening formed in the second sheet of the first pouch adjacent the closed top thereof, removable resilient clamping means for closing the open bottom of the first pouch, a second pouch formed from flexible synthetic resin sheet material and having a gas inlet opening therein, and coupling means for releasably mounting the second pouch on the first pouch and providing a sealed gas flow path between the gas outlet opening of the first pouch and the gas inlet opening of the second pouch, the mounting means including first and second coupling means mounted on the first and second pouches, respectively, cooperating connector means on the first and second coupling means capable of being connected together to releasably mount the second pouch on the first pouch and establish a closed gas flow path from the first pouch to the second pouch, and valve means in the first and second coupling means for closing the gas outlet opening and the gas inlet opening when the second pouch is not mounted on the first pouch.

12. The colostomy appliance according to claim 11 wherein the valve in the coupling member on each pouch comprises resilient means normally biasing the valves to the closed position.

13. The colostomy appliance according to claim 12 further comprising means for opening the valves in the coupling members on each pouch when the coupling members are releasably connected together.

14. The colostomy appliance according to claim 11 wherein the resilient means effectively seals the coupling means to prevent the escape of gas therefrom when the coupling members are releasably connected together.

15. The colostomy appliance according to claim 11 wherein the outlet opening in the first pouch is located between the inlet opening and the closed top.

16. The colostomy appliance according to claim 11 wherein the second pouch has an open bottom end, and further comprising removable resilient clamping means for closing the open bottom end of the second pouch.

17. The colostomy appliance according to claim 11 wherein the attaching means comprises an annular ring of adhesive material surrounding the inlet opening and bonded to the outer surface of the first sheet of the first pouch, the adhesive material being capable of adhering directly to the skin of a person using the appliance.

* * * * *